US012751842B2

(12) United States Patent
Pawlik et al.

(10) Patent No.: US 12,751,842 B2
(45) Date of Patent: Oct. 6, 2026

(54) PROSTHETIC SOCKET SYSTEM, AND PROSTHETIC SOCKET AND LINER

(71) Applicant: OTTO BOCK HEALTHCARE PRODUCTS GMBH, Vienna (AT)

(72) Inventors: Roland Pawlik, Vienna (AT); Fabian Osswald, Pfaffstätten (DE); Alexander Naescher, Eschen (LI)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 942 days.

(21) Appl. No.: 18/004,713

(22) PCT Filed: Jul. 8, 2021

(86) PCT No.: PCT/EP2021/069014

§ 371 (c)(1),
(2) Date: Jan. 9, 2023

(87) PCT Pub. No.: WO2022/008665

PCT Pub. Date: Jan. 13, 2022

(65) Prior Publication Data

US 2023/0320874 A1 Oct. 12, 2023

(30) Foreign Application Priority Data

Jul. 10, 2020 (DE) ..................... 10 2020 118 258.9

(51) Int. Cl.
*A61F 2/78* (2006.01)

(52) U.S. Cl.
CPC .... *A61F 2/7812* (2013.01); *A61F 2002/7887* (2013.01)

(58) Field of Classification Search
CPC .. A61F 2/7812; A61F 2002/7887; A61F 2/78; A61F 2002/7875
See application file for complete search history.

(56) References Cited

U.S. PATENT DOCUMENTS

| | | | | |
|---|---|---|---|---|
| 10,206,795 | B2 * | 2/2019 | Pedtke | A61F 2/2814 |
| 2013/0289743 | A1 * | 10/2013 | Abu Osman | A61F 2/78 623/36 |
| 2018/0008435 | A1 * | 1/2018 | Mantelmacher | A61F 2/78 |
| 2021/0378844 | A1 * | 12/2021 | Harding | A61F 2/80 |
| 2023/0320874 | A1 * | 10/2023 | Pawlik | A61F 2/78 623/36 |

FOREIGN PATENT DOCUMENTS

WO 2010070614 A1 6/2010

* cited by examiner

*Primary Examiner* — Bruce E Snow
(74) *Attorney, Agent, or Firm* — WCF IP

(57) ABSTRACT

The invention relates to a prosthetic socket system having: a dimensionally-stable outer socket (10) having a proximal insertion opening (11) and a distal end region (12), on which outer socket a fastening element (13) for a distal prosthetic component is arranged; and a prosthetic liner (20) that can be secured in the outer socket (10) and has a distal sealing cap (21), a supporting element (30) being arranged in the outer socket (10) proximally to the distal end region (12) of the outer socket (10) and having a recess (40) for an osseointegrated coupling element (50).

13 Claims, 7 Drawing Sheets

PROSTHETIC SOCKET SYSTEM, AND PROSTHETIC SOCKET AND LINER

The invention relates to a prosthesis socket system having a dimensionally stable outer socket with a proximal access opening and with a distal end region on which a fastening device for a distal prosthesis component is arranged, and having a prosthesis liner which can be fastened in the outer socket and has a distal end cap. The invention also relates to a prosthesis liner and a prosthesis socket for use in such a prosthesis socket system.

Prosthesis components for upper and lower extremities can be attached to a residual limb or to the patient in a variety of ways so that they can be used by the prosthesis user. In addition to secure attachment of the prosthesis component to the particular stump or body part, which attachment is necessary for safe handling of the prosthesis component, another important aspect is that the prosthesis component can be worn as comfortably and permanently as possible, so that the prosthesis component is accepted by the user and used as intended. Secure attachment of the prosthesis component is not acceptable if the prosthesis component can only be worn for a short period of time. Conversely, wearing a prosthesis component comfortably is not helpful if the functionality is restricted or the safety of use is no longer ensured as a result, for example if the prosthesis component can easily and unintentionally detach from the stump.

Different concepts have been developed for fastening prosthesis components. Initially, prostheses were fastened to the stump using belts and straps. Prosthesis sockets were developed that have a cavity to accommodate the stump. The prosthesis sockets could also be attached to the patient using straps. Prosthesis liners were developed in order to cushion the stump. These are made of a flexible, elastic material and have what is called a pinlock attached to their distal end in order to achieve mechanical locking to the prosthesis socket. A further development in prosthesis socket technology provides for the fastening of the prosthesis socket using a vacuum that is applied between the prosthesis liner, which is provided with an adhesive coating on the inside, and the prosthesis socket. This vacuum socket technology as an adhesion mechanism is also used without a prosthesis liner.

All of these systems have their advantages and disadvantages. In particular, they are relatively heavy on account of the large number of components used. The skin on the stump can become irritated on account of the usually closed inner surface of the prosthesis liner resting on it. Temperature regulation at the stump is made difficult, and there are also volume fluctuations over the course of the wearing period, with the result that an increased feeling of pressure or a decrease in the holding power can occur. In addition, a prosthesis socket with a prosthesis liner requires space, which is not available in the case of disarticulations, for example, and therefore causes difficulties in fitting.

Solutions were therefore sought to connect a prosthesis component, for example a prosthetic knee joint, as directly as possible to the prosthesis user. One possibility for this is to introduce an implant into a corresponding bone on which the prosthesis component is intended to be mounted. Using implants or osseointegrated coupling elements, it is possible to connect the prosthesis components directly to the bone without the prosthesis component being fastened with the interpositioning of soft tissue components. In this way, among other things, pressure sore problems at the end region of the stump can be avoided. The coupling elements are inserted into the appropriate bone, for example the femur, and anchored or cemented in place there. There are several surgical procedures for this.

One method provides for two-phase fitting. In the context of a first operation, a pure bone implant is implanted without any devices for coupling to an external prosthesis component. When the bone implant has become sufficiently incorporated, the coupling element, in the context of a second operation, is provided with an endo-exo interface that protrudes through the skin. After both operations, a rehabilitation phase lasting several weeks is necessary, in which the material inserted into the bone is initially not loaded at all and is thereafter subjected to defined pressure or tension. The loading is necessary in order to accelerate incorporation and to cause the bone structure to adapt to the loads that occur. Disadvantages of this method are the double operation and the rehabilitation phase of several months, which is associated with high costs and with a comparatively long period of immobilization of the patient. Such immobilization puts a strain on the musculoskeletal and postural apparatus of the patient as well as causing psychological stress.

The object of the present invention is therefore to make available a system with which a patient who has been provided with osseointegrative treatment can be fitted with a prosthesis as quickly as possible and remains mobile.

According to the invention, this object is achieved by a prosthesis socket system having the features of the main claim and by a prosthesis liner and a prosthesis socket for use in such a prosthesis socket system. Advantageous embodiments and developments of the invention are disclosed in the dependent claims, the description and the figures.

In the prosthesis socket system having a dimensionally stable outer socket with a proximal access opening in a distal end region, on which a fastening device for a distal prosthesis component is arranged, and having a prosthesis liner that can be fixed in the outer socket and has a distal end cap, provision is made that a support element is arranged in the outer socket proximally with respect to the distal end region of the outer socket and has a recess for an osseointegrated coupling element. Users who have just undergone surgery with an osseointegrated coupling element are usually very sensitive to touch in the region of the implant, since the direct connection of the implant to the bone, for example the femur, leads to sensations in the bone that do not otherwise occur. Therefore, the new prosthesis socket system is provided with a recess for an osseointegrated coupling element, which prevents loads from being passed on into the region of the implanted coupling element. With the system, it is possible for a patient, who has had a coupling element implanted, to be fitted very quickly with a prosthesis, and for a conventional prosthesis component, for example a joint, in particular a knee joint, or another prosthesis component to be arranged on the socket. This avoids inpatient stays in rehabilitation centers, the prosthesis user can return to a familiar and normal environment and can become accustomed as early as possible to using the prosthesis component. During the period of healing or incorporation, the direct introduction of compressive or tensile forces via the socket onto the implant is prevented or at least substantially reduced by the recess. The implant is also protected from mechanical contact. The patient remains active, or is immobilized for only a short time, thereby avoiding the negative effects of conventional fitting.

The support element can be arranged in the outer socket, in particular fastened or formed therein. A distance and a free space are thus created between the support element and the distal end region of the outer socket, such that the stump is not completely contacted in the region of the coupling element. The support element can be formed as an integral part of the outer socket. Alternatively, the support element can be fastened to the outer socket, in particular attached to the inside of the outer socket, such that a distance is formed between the distal end region of the outer socket and the pressure-sensitive region, in particular the region in which the bone would absorb compressive forces along the longitudinal extent. Alternatively, the support element can be arranged or formed in the prosthesis liner. The free space in the prosthesis liner is designed and located accordingly in order to keep the pressure-sensitive region of the stump fitted with the implant free and to relieve it from compressive forces.

The support element can be designed as an elastic element, as a flexible hollow body, as a frame or as a plate, with the recess being able to be designed as a through-hole, cavity or free space. The design as an elastic element has the advantage of cushioning, while a flexible hollow body also facilitates the adaptation of the support element to the outer contour of the stump or of the stump provided with a prosthesis liner. A frame enables easy and simple mechanical support within the outer socket, whereas a plate has a larger contact surface and thus exerts less surface pressure on the distal end region of the stump.

The support element can have a bearing region for the end cap, which bearing region is embodied in such a way that it can be changed in terms of its location or position, or it is fixed. The bearing region can be variably arranged or mounted both in the proximal-distal direction and also within a plane perpendicular to the longitudinal extent of the outer socket or of the prosthesis liner. A rotatable mounting is also possible, which further increases the customization options. The support element can be designed and/or mounted such that it can be displaced in all orientations or only in some of the orientations described above. For example, the bearing region or the entire support element can be rotatably/or displaceably mounted in or on the outer socket or the prosthesis liner in order to facilitate an individual adaptation of the prosthesis socket system to the respective user and, if necessary, to be able to change the position of the bearing region or of the support element in the course of the use of the prosthesis system. With such a construction, the position of the support element and/or of the bearing region can be adapted to the healing progress.

An adjustment device for adjusting the distance between the bearing region and the distal end region can be arranged on the support element. The adjustment device can, for example, enable a longitudinal displacement and can be designed in the form of a rail or several rails or rail guides. The support element is then displaceable along these rails or rail guides and can be fixed in the desired position. The fixing can take place via form-fit elements, for example by means of pins, hooks, clamps, screws or hook-and-loop fasteners. The locking can also take place on the outside of the outer socket, for example by guiding a strap with a corresponding form-fit element onto the outside and locking it there on a hook, a projection or on a corresponding component of a hook-and-loop fastener. The adjustment device can also be designed as a thread, such that an adjustment in the longitudinal extent of the prosthesis socket, i.e. in the proximal-distal direction, is made possible and a displacement toward or away from the distal end region can be effected. The adjustment device can be designed as a threaded pin, which is arranged substantially centrally inside the outer socket. Alternatively, the thread can be arranged or formed on the outer circumference of the support element and can engage with a corresponding threaded portion on the outer socket. A frame or a plate can be guided in a corresponding thread, and the position of the support element is secured, against unwanted adjustment, by suitable securing elements or safety measures, for example by insertion of wedges, clamps or pins that impede or prevent relative displacement to the outer socket.

The osseointegrated coupling element can protrude from the stump. Direct contact of a stump, freshly provided with the implant, on the support element may be undesirable due to existing sensitivities. The prosthesis liner, which is then pulled over the stump, therefore provides a through-opening for the osseointegrated coupling element, which protrudes over the stump, such that the coupling element projects into the through-opening or protrudes through the prosthesis liner and projects distally beyond the end cap or the distal end of the prosthesis liner. The coupling element is designed in particular as a pin and is provided with devices for connecting a further prosthesis component or coupling device. The introduction of a through-opening in the region in which the implanted component protrudes from the stump enables cost-effective production of the prosthesis liner while ensuring gentle treatment of the patient. The prosthesis liner with such a through-opening in the distal end cap is particularly advantageous for reducing the pressure on the swollen stump in the context of postoperative secondary treatment of the stump. The through-opening is dimensioned in such a way that a pin or a similar osseointegrated component can pass through it. The liner can be used even if there is no component penetrating the skin and protruding beyond the distal end of the stump. The liner advantageously tapers toward the edge of the opening. The material thickness of the prosthesis liner decreases toward the edge of the opening, such that little or no shoulder is formed at the edge of the opening, thereby avoiding or reducing pressure sores when an axial load is applied to the stump.

The prosthesis liner with an opening in the distal end cap is an invention in its own right.

In one development, the distal end of the coupling element is coupled to a pressure sensor. The pressure sensor can be arranged on the support element, a separate holding device or on the coupling element and is used to detect the compressive forces that occur during use and are exerted on the coupling element. In order not to disturb the process of incorporation, it may be necessary to provide a graded loading program in which a low load is initially applied to the newly treated bone. As healing progresses, the load can be gradually increased. On account of the compressive loading, the bone structure adapts to the respective load and enables the coupling element to be fixed in a stable and resilient manner in the bone.

The pressure sensor can be coupled to an acoustic, optical and/or tactile feedback device, which gives the respective user or also the physician, therapist or orthopedic technician feedback as to whether a load limit has been reached or exceeded. The sensor can also be coupled to a recording device in which the loads occurring over the period of use are recorded. The evaluation can be carried out by the user or the physician or orthopedic technician. If too great a compressive force or too great a load is applied to the coupling element, then, for example, the recess can be enlarged, the distance to the distal end region of the outer socket can be increased, or another support element can be used, or the existing support element can be positioned differently. This makes it possible to accompany and monitor the healing progress. The physician, therapist or orthopedic technician is no longer r reliant on subjective feedback and can instead make adjustments to the prosthesis socket system on the basis of objective measurement data.

In one development, provision is made that a stop as a bearing e osseointegrated coupling element is arranged in the outer socket and/or on the support element. Defined forces can be applied to the coupling element via the stop. The stop can be adjustable and/or resilient and/or resiliently mounted. The adjustability f the stop enables basic adaptation to different patients, degrees of healing progress, implantation situations or other needs. A resilient design or mounting of the stop makes it possible to set or make available a force limitation, such that a maximum force on the coupling element is not exceeded.

The prosthesis liner and the outer socket can be coupled to each other by force-fit engagement, in particular via a vacuum system and/or a magnet system. The end cap of the prosthesis liner can have a through-opening for a coupling element or a support element with a recess for receiving the coupling element. Magnets or ferromagnetic parts can be arranged on the end cap in order to enable a force-fit coupling via a magnet system to the outer socket.

The prosthesis socket for a prosthesis socket system as described above can, for example, be designed to be hinged in order to be able to adapt to different stump diameters. The prosthesis socket as an outer socket can also be used without a prosthesis liner. The use with a liner increases wearing comfort. To relieve the distal stump region during use without a liner, it is necessary for a support element, as described above, to be arranged in the prosthesis socket.

Exemplary embodiments of the invention are explained in more detail below with reference to the attached figures, in which.

Figure 1:
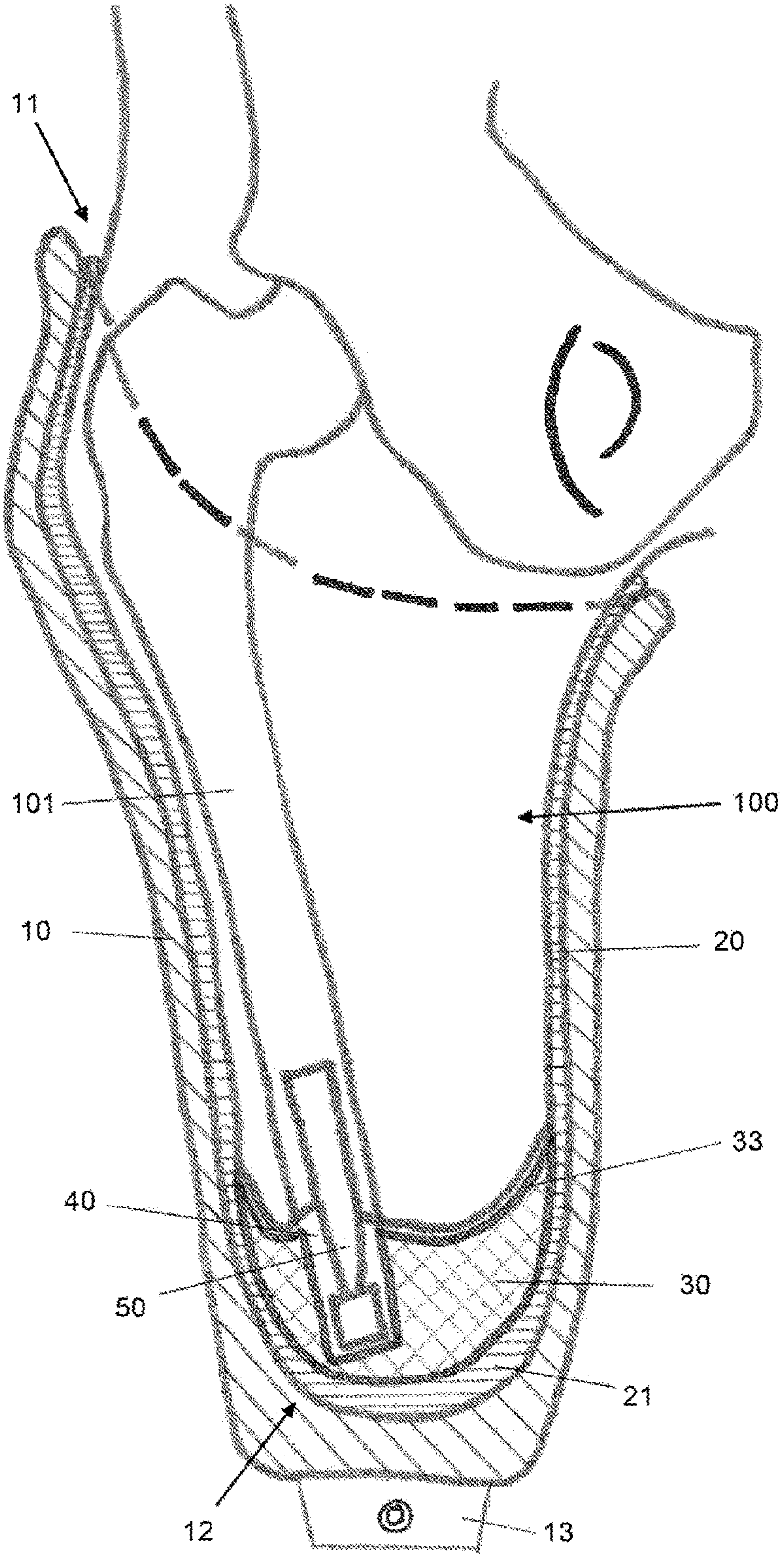
FIG. 1 shows a first embodiment of a prosthesis socket system with a support element in a prosthesis liner.

FIG. 1 is a schematic sectional representation of a prosthesis socket system with a dimensionally stable outer socket 10, which has a proximal access opening 11 and a closed, distal end region 12. A fastening element 13 for fastening a further prosthesis component, for example a prosthetic knee joint or an adapter tube or another prosthetic device, is arranged on the distal end region 12. In the exemplary embodiment shown, the prosthesis socket 10 is designed as a thigh socket which circumferentially surrounds the stump 100 of the patient's limb. Located within the stump 100, the femur 101 is surrounded by soft tissue. A coupling element 50 is implanted in the femur 101, which coupling element 50, in the exemplary embodiment shown, protrudes through the skin of the stump 101 and projects distally beyond the stump 100. The stump 100 is surrounded by a prosthesis liner 20 which is made from a flexible, in particular elastic material, for example silicone, or at least has such a material. The prosthesis liner 20 serves to cushion the stump 100 and is worn inside the prosthesis socket 10. The prosthesis liner 20 thus forms the interface between the stump 100 and the prosthesis socket 10. A support element 30 is arranged inside the prosthesis liner 20, which has a proximal access opening and a distal end cap 21, the latter being closed in the exemplary embodiment shown. Magnets or ferromagnetic parts 23 can be arranged on the end cap 21 in order to enable a force-fit coupling via a magnet system to the outer socket 10. The support element 30 can be inserted into the prosthesis liner 20. It is also possible for the support element 30 to be fastened in the prosthesis liner 20. In the exemplary embodiment shown, the support element 30 has a contact face 33 which is designed to bear directly on the distal end of the stump 100. In the region in which the coupling element 30 protrudes from the stump 100, there is a recess 40 in the support element 30, which recess 40 is designed in such a way that the entire coupling element 50 protruding from the stump 100 is accommodated therein, without a compressive force directed in the longitudinal extent of the coupling element 50 or the femur 101 being exerted thereon.

The support element 30 can exert a cushioning effect and can be elastic, or at least flexible, in order to be able to conform to the outer contour of the stump 100 and the inner surface of the prosthesis liner 20 or the prosthesis socket 10. The recess 40 prevents compressive forces from being exerted directly on the coupling element 50 during use of the prosthesis socket 10, so that a patient with an osseointegrated fixture can be equipped with a prosthetic knee joint at a very early stage. This avoids the user being kept immobile over a long period of time and having to wait for the healing phase of the coupling element 30 to be completed.

In the exemplary embodiment shown, the coupling element 50 is designed in such a way that the portion located inside the femur 101 is formed in one piece with a portion penetrating the skin. In an alternative embodiment of another fitting method, an anchor element is first cemented inside the bone, with the anchor element not penetrating the skin. Only after complete healing is a penetration element coupled to the anchor element. This requires a second operation. Even during the first phase of the operation, which includes implanting the anchor element, it may be necessary to keep the patient mobile. The recess 40 does not then have to be so deep; it is sufficient that the recess 40 is relieved of any load within the region in which the coupling element or the part of the coupling element is arranged within the bone. This occurs because the recess 40 is designed as a depression or a region that does not come into contact with the skin surface in the region in which the bone 101 or the anchor element or later the protruding coupling element 50 is located.

As an alternative to a solid design of the support element 30, the latter can be designed as a hollow body, for example as an inflatable cushion with a corresponding recess 40.

The prosthesis liner 20 in the exemplary embodiment shown has a closed contour with an access opening 11. The prosthesis liner 20 is fastened in the prosthesis socket 10 either mechanically via locking elements or in particular by the formation of a negative pressure between the outside of the prosthesis liner 20 and the inside of the prosthesis socket 10. A combination of mechanical fastening elements and a vacuum-based fastening of the prosthesis socket 10 to the prosthesis liner 20 can also be implemented. The inside of the prosthesis liner 20 rests on the skin surface of the stump 100 over as large an area as possible. The inside can be designed with ventilation channels or similar devices in order to be able to transport moisture and heat away. The support element 30 can be formed from a foam material or can have regions that have different resilience.

Figure 2:
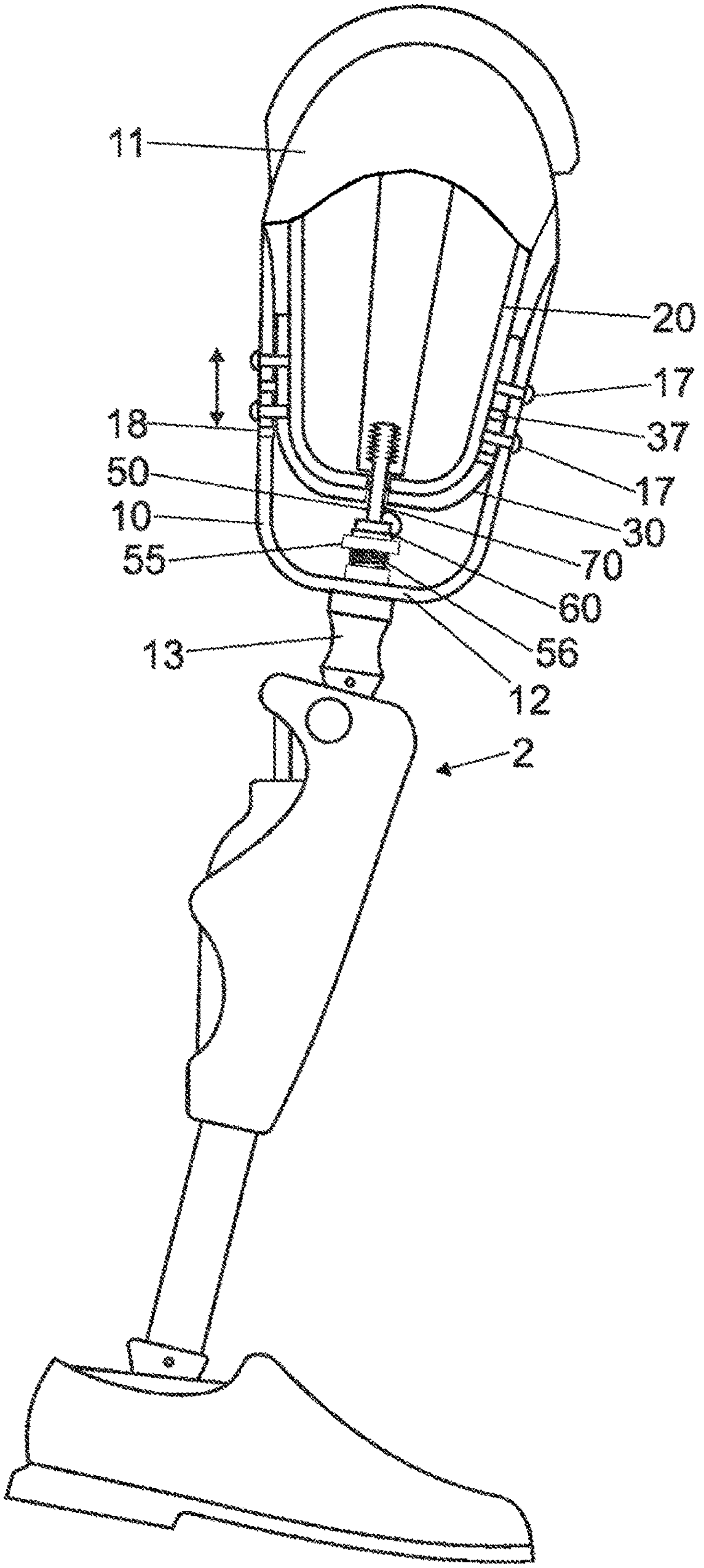
FIG. 2 shows a schematic sectional view through a second embodiment of the prosthesis socket system.

A variant of the invention is shown in FIG. 2, in which a schematic sectional view of a prosthesis socket system with a prosthesis socket 10 is shown, at the distal end of which a distal prosthesis component 2 is attached to the fastening means 13. The distal prosthesis component 2 has a prosthetic knee joint with a lower-leg tube and with a prosthetic foot attached to the latter. The prosthesis socket 10, as a thigh socket, is equipped with a proximal access opening 11 and a distal end region 12. Mounted within the prosthesis socket 10 is a support element 30 in the form of a plate or shell which is fixed in the prosthesis socket 10, at a distance from the distal end region 12 of the prosthesis socket 10. The prosthesis liner 20, which bears on the surface of the stump 100, is supported on the support element 30.

As in the embodiment according to FIG. 1, the patient is provided with a coupling element 50 which protrudes beyond the distal end of the stump 100. In the exemplary embodiment shown, there are no further components between the prosthesis liner 20 and the stump 100. The prosthesis liner 20 has a through-opening 22 through which the coupling element 50 can protrude. A recess 40 is likewise formed in the support element 30, such that the coupling element 50 implanted in the femur can protrude into a free space between the distal end of the support element 30 and the distal end region 12 of the prosthesis socket 10. A pressure sensor 60 is arranged at the distal end 51 of the coupling element 50 and is coupled to a feedback device 70 in the form of a signal generator, for example an optical, acoustic or tactile signal generator. In addition, the pressure sensor 60 can be equipped with a sensor device in order to transmit the sensor data to an evaluation device. The pressure sensor 60 can also be coupled to a data processing device with an integrated memory unit and interface, in order for load data to be recorded, forwarded, evaluated or the like.

In the exemplary embodiment shown, the distal end 51 of the coupling element 50 is supported, by way of the pressure sensor 60, on a stop 55 which is supported via a spring 56 on the distal end region 12 of the prosthesis socket. The spring 56 serves as a force limiter and the spring preload can be adjusted such that a controlled compressive force can be exerted on the distal end 51 of the coupling element 50. The main load when walking is transferred via the prosthesis socket 10 and the support element 30 to the prosthesis liner 20 and from there to the soft tissue components of the stump 100. A loading of the coupling element 50 by compressive force occurs only to the extent that is desired and necessary as part of the healing progress. The adjustability of the spring 56 makes it possible to take into account the individual sensitivities of the patient, for example to initially exert lower compressive forces in the case of a high degree of sensitivity.

In order to be able to ensure basic adjustability of the prosthesis socket system and possibly also of the load that is exerted on the coupling element 50, the support element 30 is arranged displaceably within the prosthesis socket 10. For this purpose, fastening means 17 in the form of bolts or screws are arranged in the prosthesis socket 10 and engage in corresponding recesses within the support element 30. It is also possible for several through-holes 18 to be arranged within the prosthesis socket 10, which are arranged at a vertical distance from one another. In addition, it is possible to position the support element 30 within the prosthesis socket 10 at different levels and at a different distance from the distal end region 12. It is also possible to arrange the through-holes 18 in the prosthesis socket 10 or the threads 37 in the support element 30 offset over the circumference, such that a rotation of the support element 30 within the holder 10 is possible. As a result, when the recess 40 is arranged in the support element 30 eccentrically to an axis of rotation, the positioning of the recess 40 can be individually adapted.

Figure 3:
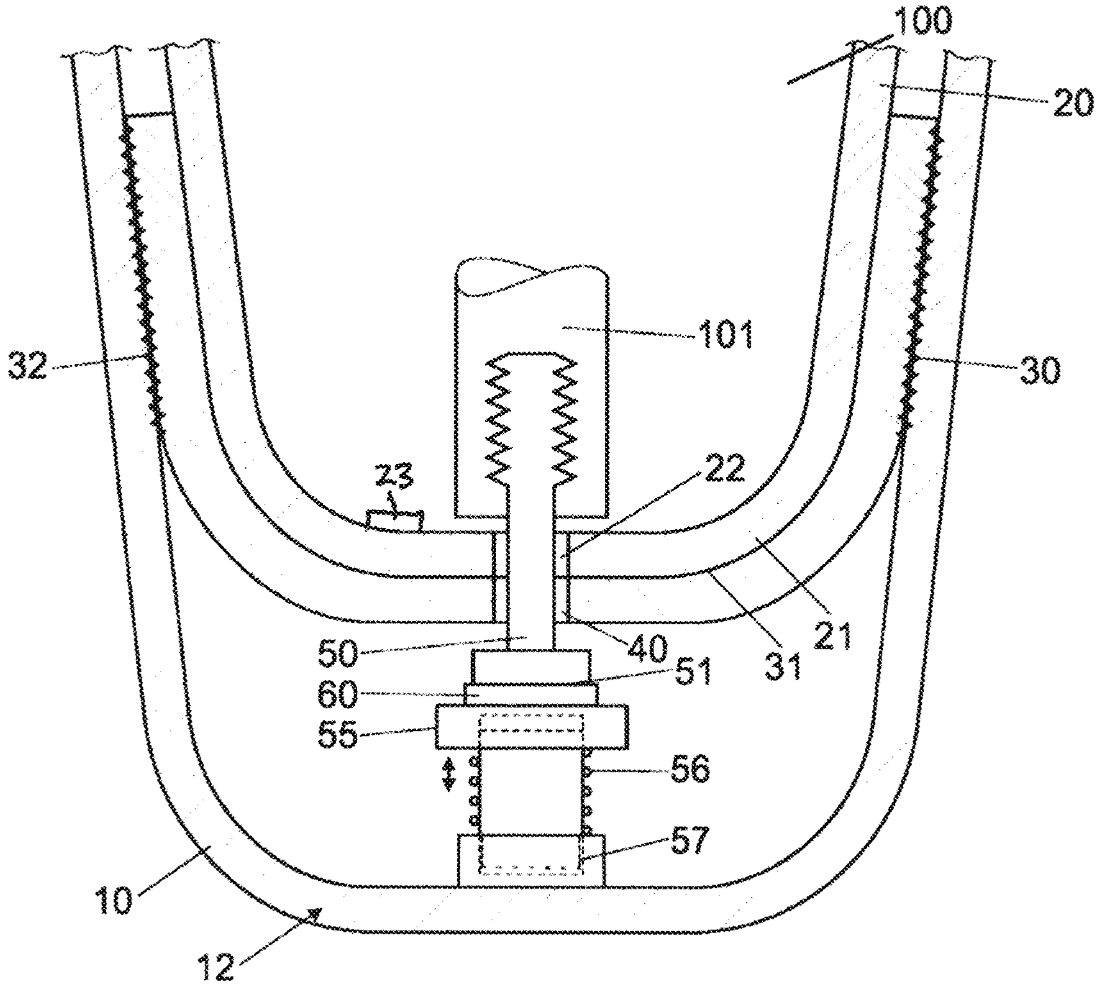
FIG. 3 shows a detailed representation of a variant of FIG. 2.

FIG. 3 shows a variant of the prosthesis socket system according to FIG. 2 in an enlarged view, the basic structure corresponding to that of FIG. 2. Instead of the screws 17 and the through-openings 18 or threads 37 for adjusting the distance between a bearing region 31 on the spacer element 30 and the distal end region 12, in the embodiment according to FIG. 3 an external thread 32 is formed or arranged as an adjustment device 32 on the outer circumference of the support element 30. The external thread 32 engages with an internal thread which is arranged or formed on the inside of the prosthesis socket 10. By turning the support element 30 in one direction or the other, it is possible to change the distance between the bearing region 31 and the distal end region 12 and thus also the stop 55 or to change the pretensioning of the spring 56.

In the embodiment according to FIG. 3, the spring 56 is arranged around a pin which has, at its distal end, a thread 57 which is screwed into a corresponding thread in a holder. By turning the pin, it is possible to change the effective length of the pin and to adjust the height of the stop 55. A recess is formed within the stop 55, such that the stop 55 can be displaced as a plate against the spring 56 along the double arrow. The sensor 60 is arranged between the stop 55 and the distal end 51 of the coupling element 50 in order to detect the compressive forces actually acting on the coupling element 50 in the direction of the femur 101. The sensor 60 is coupled to a data processing device (not shown), possibly also to the feedback device 70, in order to provide the user or the orthopedic technician or physician with feedback on how the load is during use and whether an adjustment of the stop 55 and/or of the spring 56 is necessary or whether the distal end 51 of the coupling element 50 must be removed from the stop 55 via the adjusting device 32 or can be moved toward it.

Figure 4:
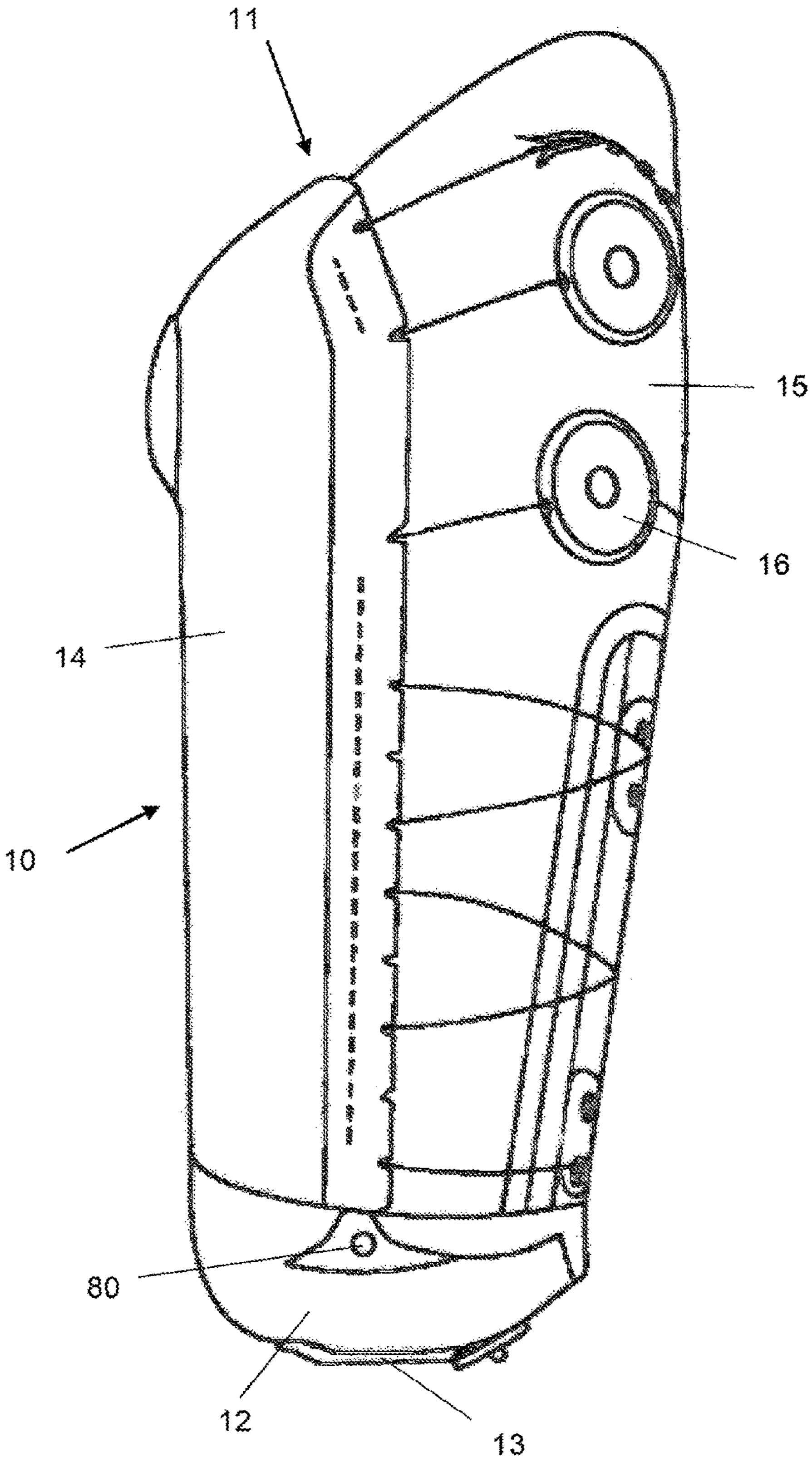
FIG. 4 shows a prosthesis socket in a side view.

FIG. 4 shows a prosthesis socket 10 in a side view. The prosthesis socket 10 can be part of a prosthesis socket system as described above. The fastening element 13 for coupling a distal prosthesis component is arranged at the distal end of the prosthesis socket 10. The distal end region 12 is designed as a closed cap, from which two prosthesis socket shells 14, 15 extend in the proximal direction. The prosthesis socket shells 14, 15 overlap each other and their circumference can be moved toward each other and away from each other via a closure system 16 or a tensioning system. In the exemplary embodiment shown, the closure system 16 works via tension elements; other clamping devices or closure devices can likewise be arranged on the prosthesis socket 10 in order to change the circumference of the prosthesis socket 10 and adapt it to the respective user. At least one of the prosthesis socket shells 14, 15 can be mounted on the distal end region so as to be pivotable about a pivot axis 80.

Figure 5:
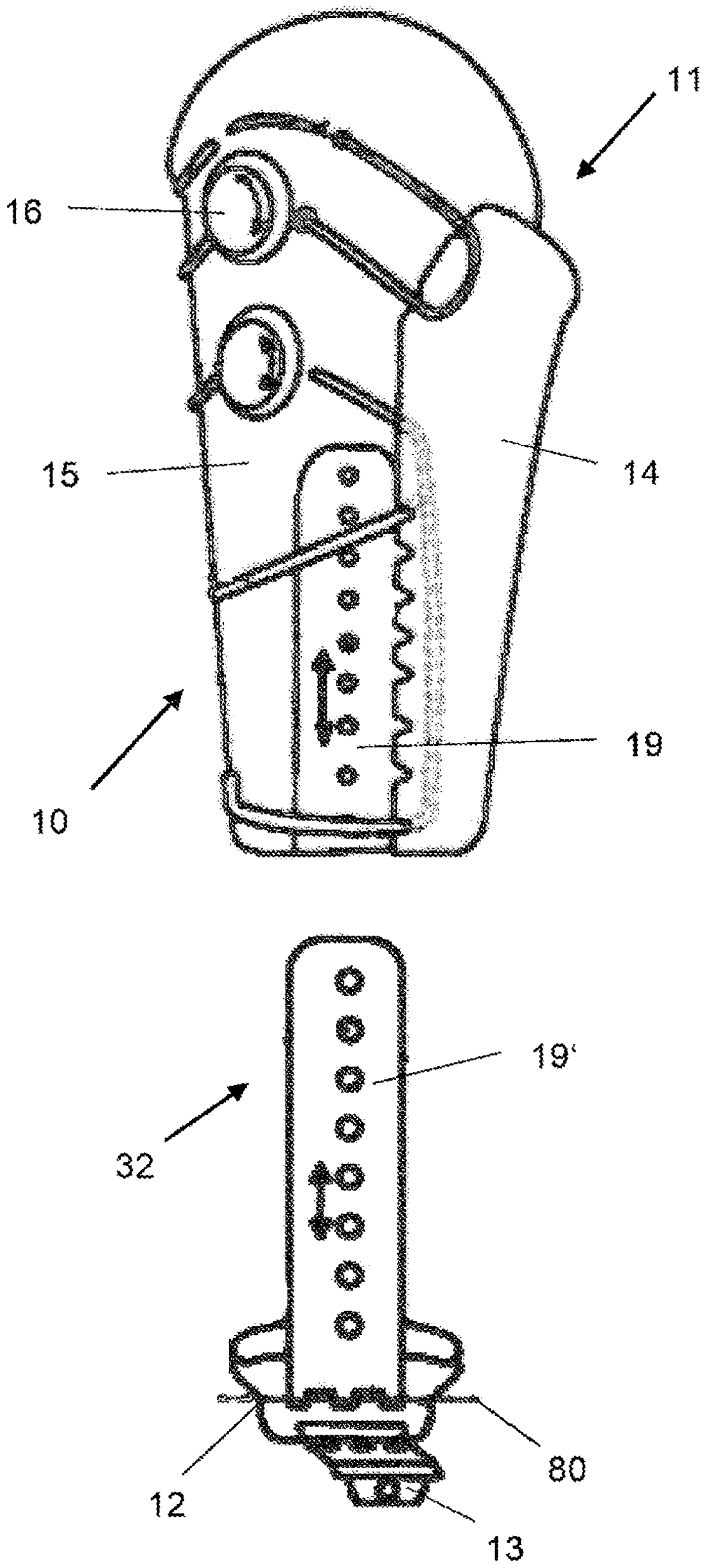
FIG. 5 shows a height-adjustable prosthesis socket.

FIG. 5 shows a further variant of a prosthesis socket 10. Here too, two prosthesis socket shells 14, 15 can be moved toward each other and away from each other via a closure system 16 or a clamping system, in order to be able to set different distances from each other. The distal end region 12 is designed as a separate component, from which rails 19' extend in the proximal direction. The rails 19' are mounted on the distal end region 12 so as to be pivotable about a pivot axis 80 and can be inserted into guides 19 which are arranged or formed on at least one of the prosthesis socket shells 14, 15. An adjustability in length of the entire prosthesis socket 10 can be achieved by means of bores or threads arranged at distances from one another in the longitudinal extent.

For this purpose, the rails 19' are inserted into the guides 19 as far as is necessary so that the distal end region 12 has the correct distance from the coupling element or support element, which is not shown. Permanent locking of the distal end region 12 to the prosthesis socket shells 14, 15 is then effected by means of screws, bolts or the like. An adjustment of the circumference is achieved by the closure system 16.

Figure 6:
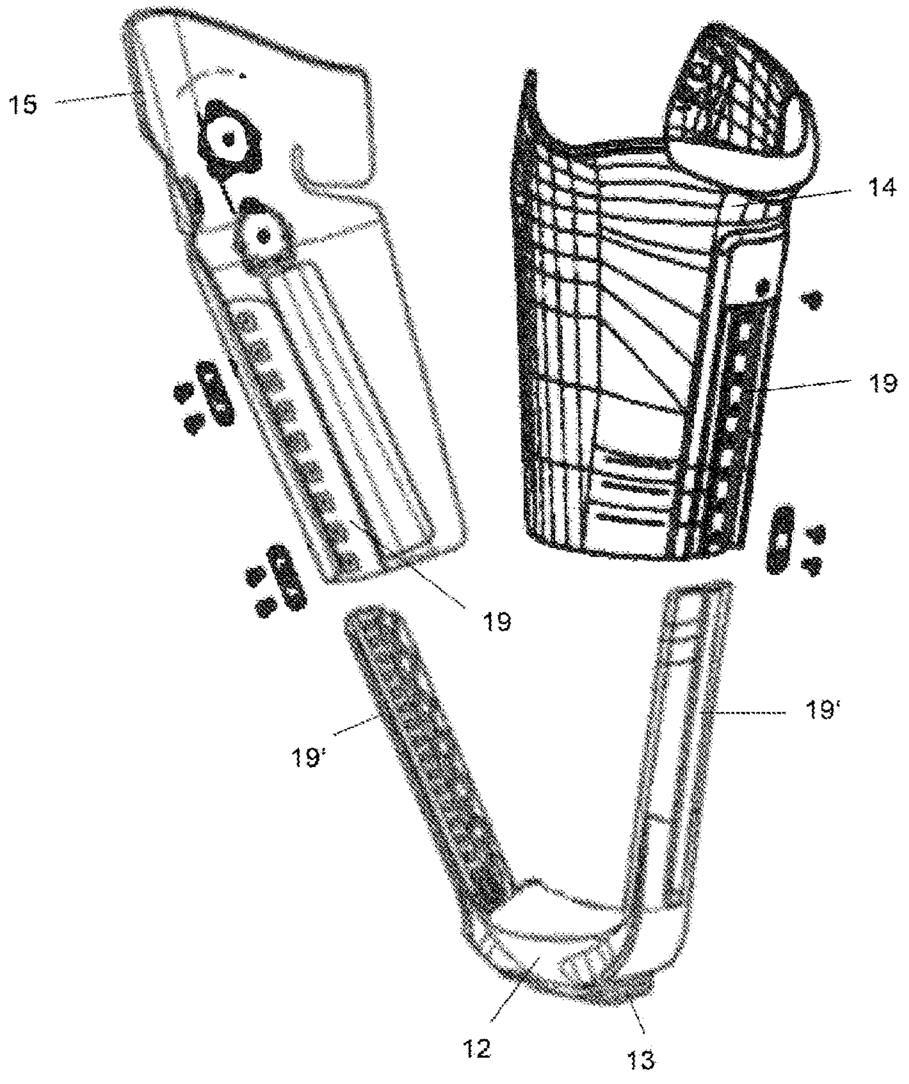
FIG. 6 shows a hinged prosthesis socket.

FIG. 6 shows a variant of the prosthesis socket 10. The distal end region 12 with the fastening element 13 arranged thereon forms a clasp together with the two rails 19', the two prosthesis socket shells 14, 15 being slipped onto the rails 19' and being fixed at the appropriate position along the rails 19' using screws.

Figure 7:
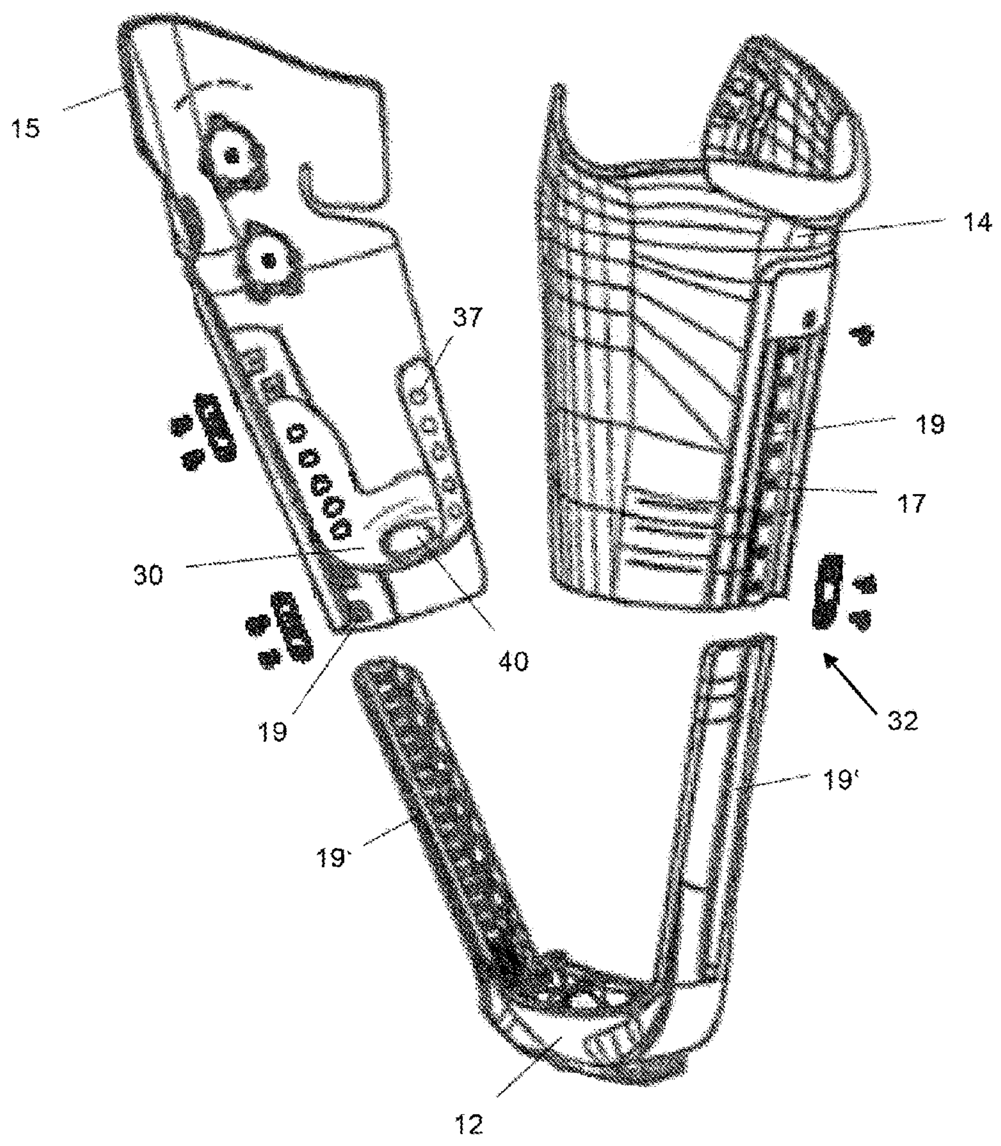
FIG. 7 shows a hinged prosthesis socket with adjustable support element.

FIG. 7 shows a variant of the design of the prosthesis socket 10 of FIG. 6, with a support element 30 attached to the inside of the prosthesis socket shells 14, 15. The support element 30 is cup-shaped and has a central recess 40 so that no pressure is exerted directly on the region of the coupling element 50 or of an implanted component of the coupling element 50. The support element 30 can be fixed along the length of the prosthesis socket 10 at different locations within the prosthesis socket shells 14, 15 or the rails 19'. For this purpose, the support element 30 has tabs or strips of material with recesses or threads 37 into which the screws or bolts for fixing the prosthesis socket shells 14, 15 to the rails 19' can likewise be inserted. Should a different position be necessary, the support element 30 can also be fixed separately using screws in the holes provided for this purpose in the rails 19'.

The invention claimed is:

1. A prosthesis socket system, comprising:

a dimensionally stable outer socket with a proximal access opening and with a distal end region on which a fastening device for a distal prosthesis component is arranged, a prosthesis liner which can be fastened in the outer socket and has a distal end cap, and a support element arranged in the outer socket proximally with respect to the distal end region of the outer socket wherein the support element has a recess for an osseointegrated coupling element, wherein the support element has a bearing region for the end cap, which bearing region is configured to be changeable in position, wherein the support element is assigned an adjustment device for adjusting a distance between the bearing region and the distal end region.

2. The prosthesis socket system as claimed in claim 1, wherein the support element is configured as an elastic element, as a flexible hollow body, as a frame or as a plate.

3. The prosthesis socket system as claimed in claim 1, wherein the prosthesis liner has a through-opening into which the osseointegrated coupling element protruding from the stump protrudes or through which the osseointegrated coupling element protruding from the stump passes through the prosthesis liner and protrudes distally from the end cap.

4. The prosthesis socket system as claimed in claim 1, wherein a distal end of the coupling element is coupled to a pressure sensor.

5. The prosthesis socket system as claimed in claim 4, wherein the pressure sensor is coupled to an acoustic, optical and/or tactile feedback device.

6. The prosthesis socket system as claimed in claim 1, wherein a stop as a bearing for the osseointegrated coupling element is arranged in the outer socket and/or on the support element.

7. The prosthesis socket system as claimed in claim 6, wherein the stop is adjustable and/or resilient and/or resiliently mounted.

8. The prosthesis socket system as claimed in claim 1, wherein the prosthesis liner and the outer socket are coupled to each other by force-fit engagement.

9. The prosthesis socket system as claimed in claim 1, wherein the support element is fastened in the outer socket or the prosthesis liner.

10. A prosthesis liner for a prosthesis socket system comprising a dimensionally stable outer socket with a proximal access opening and with a distal end region on which a fastening device for a distal prosthesis component is arranged, and a support element arranged in the outer socket proximally with respect to the distal end region of the outer socket wherein the support element has a recess for an osseointegrated coupling element, wherein the support element has a bearing region for an end cap, which bearing region is configured to be changeable in position, and wherein the support element is assigned an adjustment device for adjusting a distance between the bearing region and the distal end region, wherein the prosthesis liner is configured to be fastenable in the outer socket of the prosthetic socket system and has a distal end cap.

11. The prosthesis liner as claimed in claim 10, wherein the end cap has a through-opening for a coupling element, or wherein the support element has a recess for receiving a coupling element.

12. The prosthesis liner as claimed in claim 10, wherein magnets or ferromagnetic parts are arranged on the end cap.

13. A prosthesis socket, comprising:

a dimensionally stable outer socket with a proximal access opening and with a distal end region on which a fastening device for a distal prosthesis component is arranged, a prosthesis liner which can be fastened in the outer socket and has a distal end cap, and a support element arranged in the outer socket proximally with respect to the distal end region of the outer socket wherein the support element has a recess for an osseointegrated coupling element, wherein the prosthesis socket is configured to be part of a prosthesis socket system wherein the support element has a bearing region for the end cap, which bearing region is configured to be changeable in position, and wherein the support element is assigned an adjustment device for adjusting a distance between the bearing region and the distal end region.

* * * * *